United States Patent [19]
Sachdeva et al.

[11] Patent Number: 6,139,316
[45] Date of Patent: Oct. 31, 2000

[54] DEVICE FOR BONE DISTRACTION AND TOOTH MOVEMENT

[76] Inventors: Rohit C. L. Sachdeva, 2605 Courtside La., Plano, Tex. 75093; Farrokh Farzin-Nia, 141 W. Fairview Blvd., Inglewood, Calif. 90302; Lawrence M. Wolford, 4556 Belfort, Dallas, Tex. 75202

[21] Appl. No.: 09/237,779

[22] Filed: Jan. 26, 1999

[51] Int. Cl.[7] .................................................. A61C 3/00
[52] U.S. Cl. ................................................. 433/7; 606/71
[58] Field of Search ............................... 433/7; 606/57, 606/60, 71, 70, 62, 63, 69

[56] References Cited

U.S. PATENT DOCUMENTS

| | | | |
|---|---|---|---|
| 5,281,133 | 1/1994 | Farzin-Nia . | |
| 5,439,377 | 8/1995 | Milanovich | 433/7 |
| 5,700,263 | 12/1997 | Schendel | 606/71 |
| 5,735,688 | 4/1998 | Razdolsky et al. . | |
| 5,885,283 | 3/1999 | Gittleman | 606/71 X |
| 5,885,289 | 3/1999 | Muller | 606/71 |
| 5,885,290 | 3/1999 | Guerrero et al. | 433/7 X |
| 5,904,479 | 5/1999 | Staples | 433/7 |

*Primary Examiner*—Nicholas D. Lucchesi
*Attorney, Agent, or Firm*—Wood, Herron & Evans, L.L.P.

[57] ABSTRACT

The present invention relates to a device for performing bone distraction and/or tooth movement, and more particularly to a widening or contracting device which is capable of effecting bone distraction in more than one plane of space simultaneously. In its broadest aspects, the present invention is a device that can be used for bone distraction or osteogenesis, as well as tooth movement, which includes an expandible (or contractible) member for affixation in the oral cavity of a patient. The device is adapted to provide distraction of a selected craniofacial bone, such as the mandible, or movement of teeth, simultaneously in more than one plane of space. The expandible (or contractible) member includes a mechanism for expanding (or contracting) the expandible (or contractible) member to achieve the desired distraction of the selected bone or movement of selected teeth.

19 Claims, 4 Drawing Sheets

DEVICE FOR BONE DISTRACTION AND TOOTH MOVEMENT

FIELD OF THE INVENTION

The present invention relates to a device for performing bone distraction and/or tooth movement, and more particularly to a widening or contracting device which is capable of effecting bone distraction in more than one plane of space simultaneously.

BACKGROUND OF THE INVENTION

Bone distraction and the associated osteogenesis is a process by which bone growth is promoted by cutting a bone and separating it in a controlled manner. As the separation of the bone at the fracture site takes place, new bone is formed in the intervening space created by the separation. Originally, this technique was developed for lengthening the long bones in the body, but was later broadened and is now applied to many parts of the body including the bones in the craniofacial area.

In particular, promoting bone growth in the jaw (mandible) has been under investigation and development for several years to address known deformities associated with the lack of bone in that region. Various surgical procedures have been developed to address bone growth in the craniofacial area and likewise, various appliances have been devised for bone distraction in the craniofacial area.

One of the most common techniques presently in use is cutting the mandible at the apex of the arch and installing a rapid palatal expander (RPE) by affixing its legs to one or more teeth on opposite sides of the palatal arch. Alternatively, the legs of known RPE's can be attached directly to the mandibular bone, or a combination of teeth and bone. The patient (or clinician) then regularly activates the device with a key (pin) which is turned a desired amount daily to achieve the widening effect. One drawback to this technique of utilizing RPE's currently on the market is that the device operates strictly in a linear manner by spreading the cut mandibular bone linearly. This linear spreading may cause the condyles to move laterally out of their sockets, which is highly undesirable. Additionally, many RPE's currently available are bulky and cannot be easily accommodated in patients who have narrow jaws, which is the reason they are undergoing the distraction osteogenesis to begin with. Furthermore, RPE's typically have sharp edges and are not designed to come into direct contact with the soft tissues of the patient's oral cavity. Moreover, the overall rigidity of the RPE may be compromised when the bone is completely distracted. Lastly, the required daily activation of the device can be particularly difficult when the device is affixed in the posterior section of the mouth.

Therefore, what is needed is an expansion (or contraction) device for patients undergoing bone distraction or tooth movement having a smooth finish and a lack of sharp edges such that it can be placed in contact with the soft tissue while expansion (or contraction) is taking place. It is further desired to have a device for use in bone distraction or tooth movement where the movement created is simultaneously in more than one plane of space.

SUMMARY OF THE INVENTION

In its broadest aspects, the present invention is a device that can be used for bone distraction or osteogenesis, as well as tooth movement, which includes an expandible (or contractible) member for affixation in the oral cavity of a patient. The device is adapted to provide distraction of a selected craniofacial bone, such as the mandible, or movement of teeth, simultaneously in more than one plane of space. The expandible (or contractible) member includes a mechanism for expanding (or contracting) the expandible (or contractible) member to achieve the desired distraction of the selected bone or movement of selected teeth. Hereinafter, references to expanding, expandible and expand should be considered to also include contracting, contractible, and contract, since the device can be used for expansion or contraction.

In one embodiment, the expanding mechanism comprises a rack and pinion and the expandible member includes a housing that is slidably engaged with the rack. Both the rack and the housing include portions which are adapted to be affixed in the oral cavity of a patient. These portions may be affixed directly to a patient's teeth, to adjacent sections of a craniofacial bone of the patient, or to combinations of a patient's tooth and the craniofacial bone of the patient.

The device has a substantially smooth finish such that it can be placed in contact with the patient's soft tissue without causing undue discomfort to the patient. This means the device may be on the lingual or labial side of the teeth, whichever is the most expedient for the given treatment.

The ability of the device to provide distraction simultaneously in more than one plane of space is due to the fact that the expandible member is either curved (singly or compound) or that the expanding mechanism itself provides movement of the device in more than one plane of space simultaneously. This latter result can be achieved, for example, by a combination rack and rotating pinion in which the interengaging teeth of the rack and pinion are non-parallel (such as conical) and therefore rotation of the pinion causes movement along a compound curve in more than a single, linear plane of space. This results in expansion along a curved line, such as the jaw line, which may take the strain off of the condyle joints of the mandible.

As an alternative to conical or other non-parallel teeth on the rack, the entire device can be curved (in one or more different planes) such that activation of the expanding mechanism causes relative movement of the selected craniofacial bone in more than one plane of space. The gear teeth on the rack and pinion may be helical, or another appropriate design, to improve the engagement and performance of the device.

These and other features and advantages of the present invention will become apparent to persons skilled in the art upon reading the more detailed description which follows, in conjunction with the drawings.

DETAILED DESCRIPTION OF THE INVENTION

Various features of specific embodiments of the present invention are shown in the accompanying drawings. As stated previously, descriptions herein of expansion and expanding members should also be considered to describe contraction and contracting members.

Figure 1:
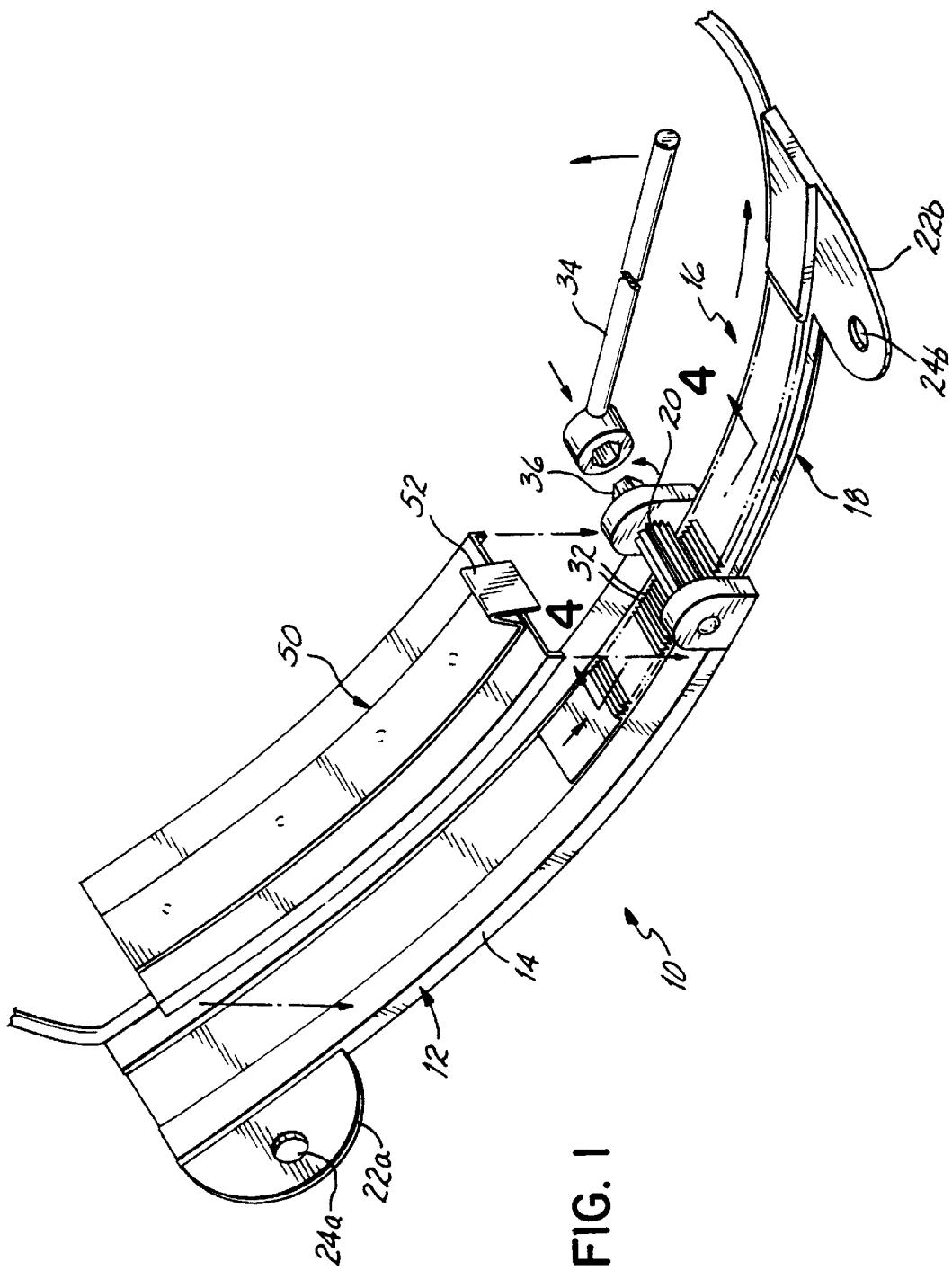
FIG. 1 is a perspective view of one embodiment of the present invention.
Figure 2:
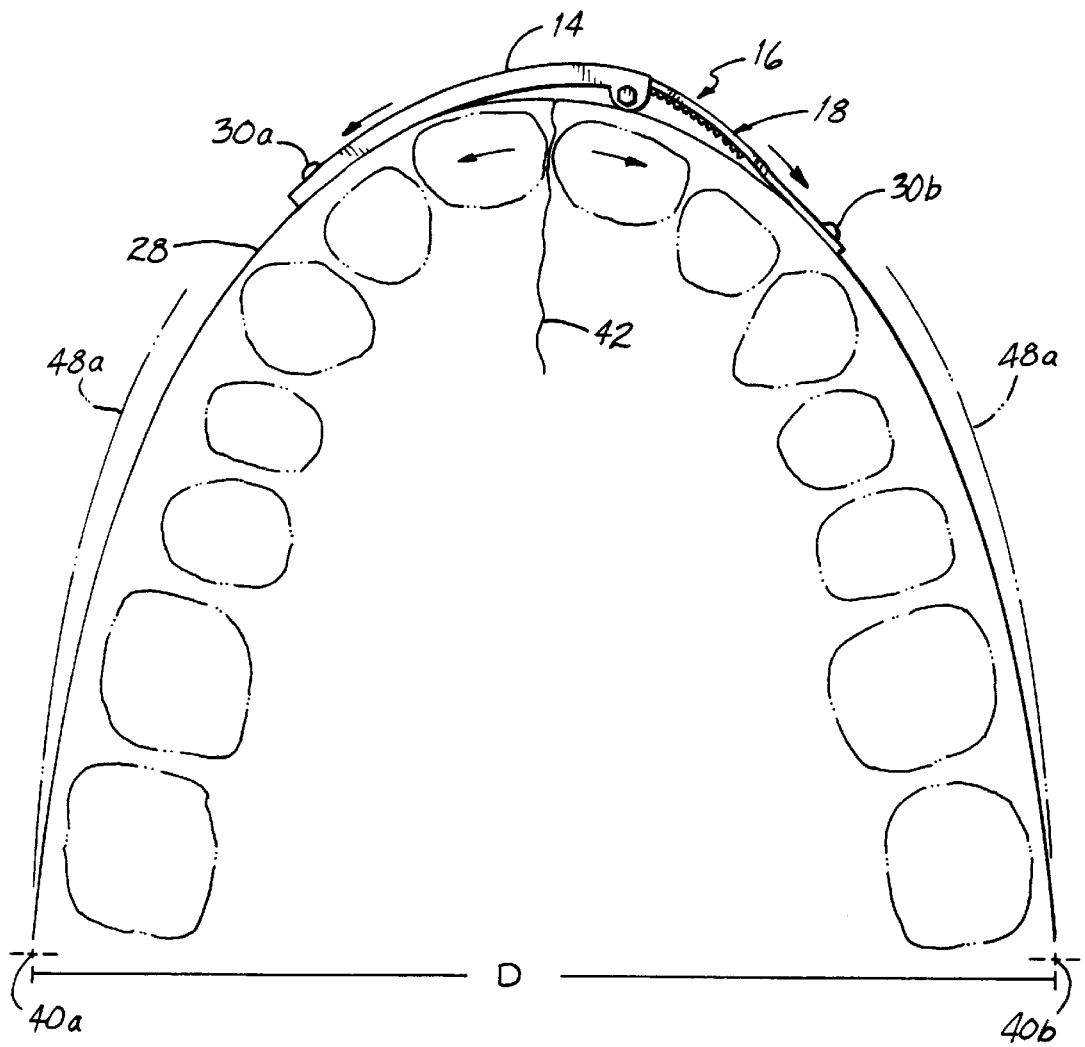
FIG. 2 is a top plan view showing the embodiment of FIG. 1 affixed to a patient.
Figure 5:
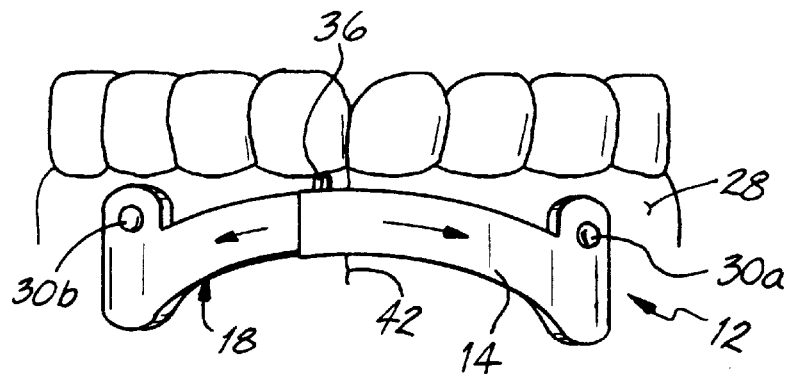
FIG. 5 is a front elevation of one embodiment of the present invention affixed to the mandible of a patient.

A preferred embodiment is shown in perspective view in FIG. 1. Generally speaking, the bone distraction device 10 of the present invention includes an expandible member 12 which itself consists of a housing 14 that is slidably engaged with an expanding mechanism 16. The expanding mechanism as shown in FIG. 1 comprises a rack 18 and pinion 20, although other mechanisms can be used. Both the rack 18 and the housing 14 are designed to be affixed in the oral cavity of a patient as for example by depending tabs 22a and 22b. Through-holes 24a and 24b facilitate affixing the housing 14 and rack 18 to a selected craniofacial bone, such as the mandible, by virtue of screws (not shown). FIGS. 2 and 5 show top and front views, respectively, of a device according to the present invention affixed to the mandible 28 of a patient. In those Figures, screws 30a and 30b are shown affixing the device to the patient's mandible.

Figure 4:
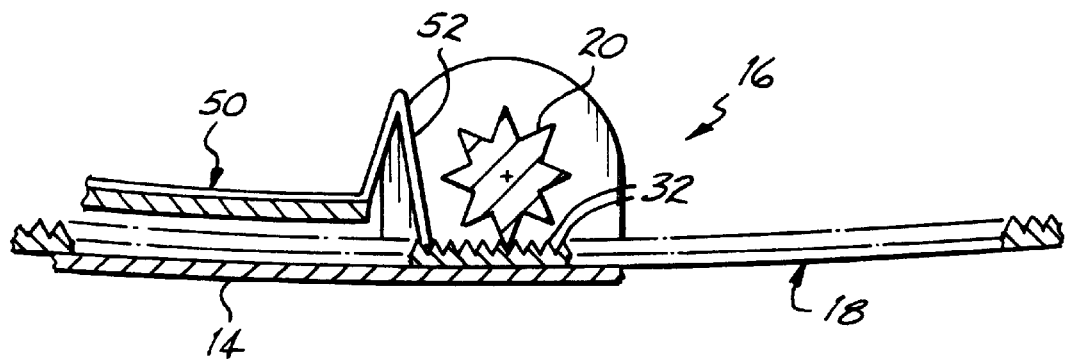
FIG. 4 is a partial cross-sectional view taken on lines 4—4 of FIG. 1.

With reference again to FIG. 1, the pinion 20 engages the teeth 32 of rack 18. This is shown in more detail in FIG. 4. A separate hex wrench 34 may be used by the patient or clinician to actuate the pinion by engaging hex head 36 which is integral with the shaft of pinion 20. By rotating hex head 36 with hex wrench 34, pinion 20 engages rack teeth 32 thereby causing expansion of the expandible member 12 by the sliding engagement between rack 18 and housing 12. By rotating in the proper direction, the expansion of the device is effectuated and by virtue of being affixed to the selected craniofacial bone of a patient, which has previously been split by an appropriate surgical technique, widening or expansion at the split in the bone is accomplished. The device of the present invention permits the periodic expansion to occur.

Figure 3:
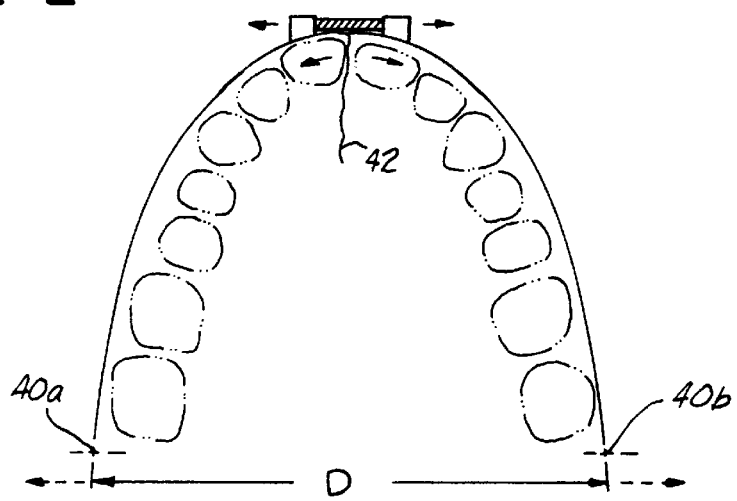
FIG. 3 is a top plan view of a prior art expansion device.

As is more clearly apparent in FIG. 2, the device of the present invention is configured so as to provide distraction of a selected craniofacial bone simultaneously in more than one plane of space. More particularly, the prior art type expansion devices are shown generally in FIG. 3. These devices operate in a purely linear manner which may cause displacement of the condyles represented by reference numeral 40a and 40b from the temporal mandibular joint (TMJ). This displacement of the condyles 40a and 40b may take place along line D shown in FIG. 3. The device can also be used for tooth movement, such as retraction or distallization of teeth as well as distraction. Further, it may have various applications for distraction of different sections of the maxilla.

As represented diagrammatically in FIG. 2, utilizing the expansion device of the present invention for bone distraction does not result in undesirable displacement of the condyles 40a and 40b. In fact due to the movement imparted by the devices of the present invention (i.e., in two planes of space simultaneously), the condyles are not displaced from the TMJ, but rather the mandible is widened at the point of distraction 42 to follow generally the dotted lines 48a, 48b shown in FIG. 2.

Again with reference to FIG. 1 and FIG. 4, the bone distraction device of the present invention preferably further includes a locking mechanism 50 which is engaged with housing 14 and has a locking extension arm 52 that engages teeth 32 of rack 18 to prevent the rack 18 from sliding relative to housing 14. The lock mechanism 50 may engage the rack 18 at either side of the pinion 20.

Figure 6:
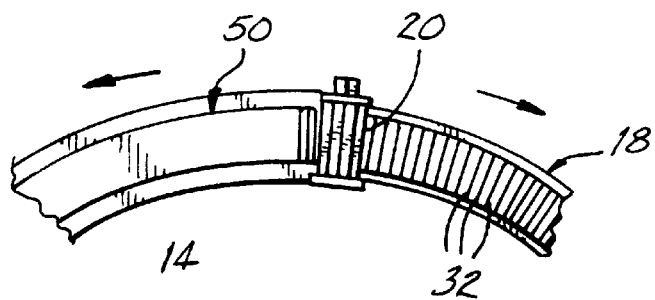
FIG. 6 is a partial rear plan view of an alternative embodiment of the present invention.

It will be appreciated that the simultaneous expansion in two planes of space is accomplished utilizing the device 10 shown in FIGS. 1 and 2 by virtue of the curvature of that device. As an alternative, the embodiment shown in FIGS. 5 and 6 is curved in an arc relative to the plane of the mandible as well as curved to follow the mandibular arch (as is true of the FIG. 1 embodiment). With specific reference to FIG. 6, due to the arcuate curvature of the embodiment shown, it may be appropriate for pinion 20 to be conically shaped and for the teeth 32 of rack 18 to likewise have a conical configuration.

Figure 7:
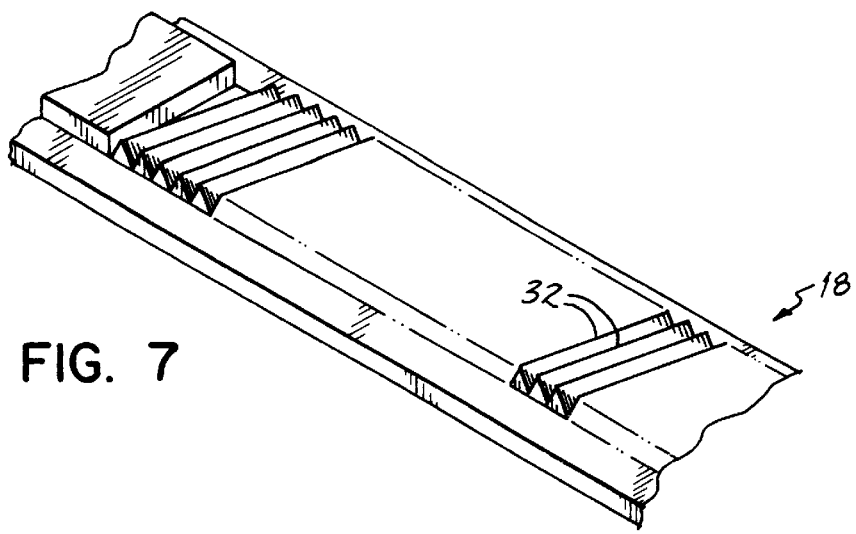
FIG. 7 is a perspective view of an alternative embodiment of the rack portion of the present invention.
Figure 8:
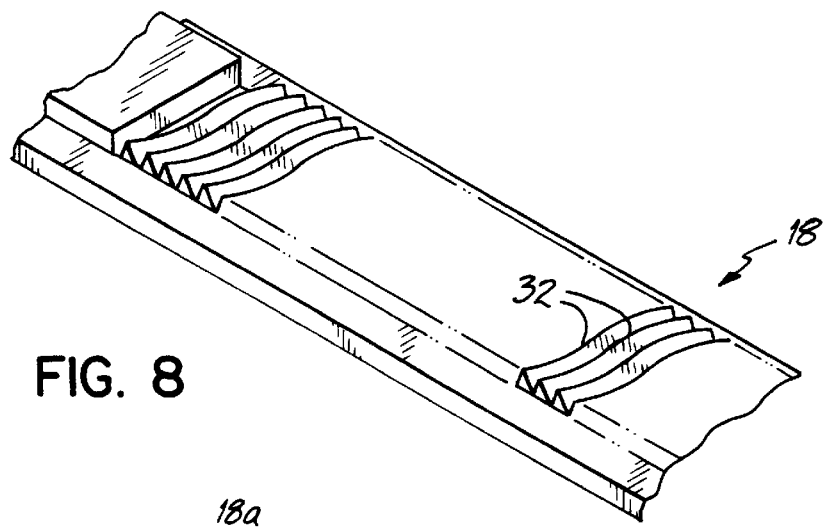
FIG. 8 is a perspective view of yet another embodiment of the rack portion of the present invention.
Figure 9:
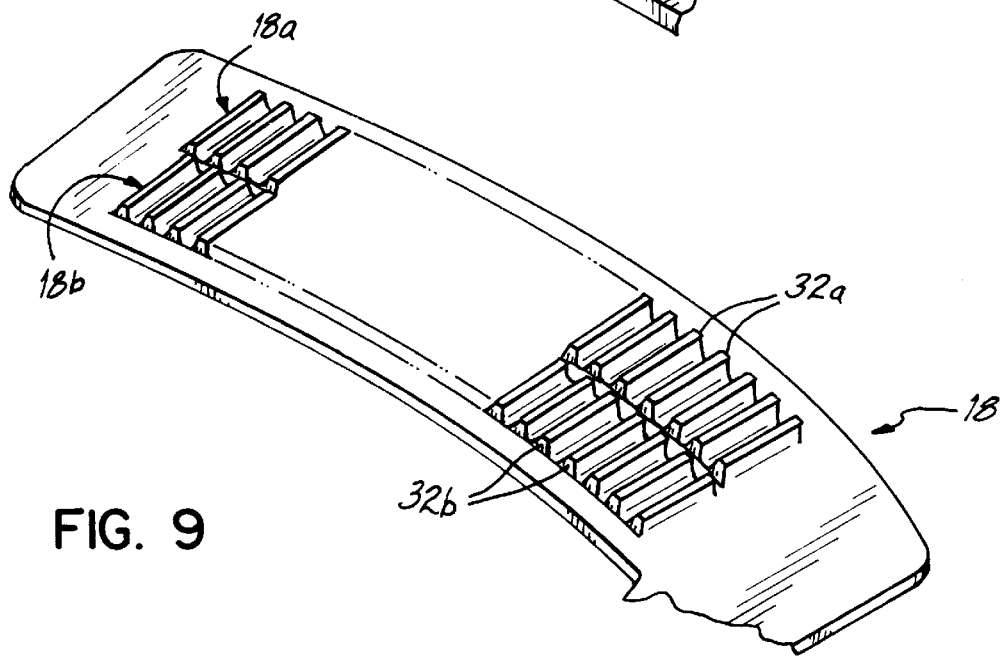
FIG. 9 is still another embodiment of the rack portion of the present invention.

Alternative rack configurations are shown in FIGS. 7, 8 and 9. In the FIG. 7 example, the teeth 32 of rack 18 are not perpendicular to the edges of the rack but rather are angled relative thereto. As will be apparent, but is not shown, the pinion associated with a rack configured as shown in FIG. 7 must have teeth that would correspond to the angled nature of teeth 32 of rack 18. Similarly, FIG. 8 shows yet another alternative configuration for rack 18. In that embodiment, teeth 32 undulate and the associated pinion (not shown) would require teeth to match. Lastly, FIG. 9 shows an alternative embodiment wherein there are two sets of rack teeth 32a and 32b. Racks 18a and 18b are offset relative to one another by the width of the one tooth and would require a pinion (not shown) that has dual sets of teeth for engagement with the offset racks 18a and 18b. It will be appreciated by persons skilled in the art that any configuration of rack and pinion can be utilized successfully in the context of the distraction device of the present invention. Therefore, the invention is not intended to be limited to the specific examples shown and described herein. Furthermore, it will be appreciated by persons skilled in the art that other mechanisms for providing expansion (or contraction) simultaneously in two planes of space are possible. Examples of actuating mechanisms other than the rack and pinion mechanism shown herein, are screw-type expanders and other mechanisms known in the art.

Having thus described the invention with reference to the accompanying drawings, it must be borne in mind that the invention is not intended to be limited to the specific structural embodiments shown and described. As stated above, numerous variations for the rack and pinion configuration are contemplated in addition to those shown herein. Furthermore, other expansion mechanisms are contemplated with the common requirement being that simultaneous movement in more than one plane of space is effectuated. Otherwise, the scope of the present invention is only limited by the claims which follow.

What is claimed is:

1. A device for bone distraction and movement of teeth, comprising:

an expandible member for affixation in the oral cavity of a patient and adapted to provide movement of a selected craniofacial bone or teeth simultaneously in more than two planes of space, said expandible member including a mechanism for expanding said expandible member.

2. The device of claim 1 wherein said expandible member is capable of contraction such that the bone or teeth movement is contraction not expansion.

3. The device of claim 1 wherein said expanding mechanism comprises a rack and pinion-type device.

4. The device of claim 3 wherein said expandible member includes a housing slidably engaged with said rack.

5. The device of claim 4 wherein said pinion is rotatably attached to said housing and operably engaged with said rack, whereupon rotation of said pinion in a selected direction causes one of expansion or contraction of said expandible member to effect the movement of a selected craniofacial bone or teeth.

6. The device of claim 5 further comprising an activator engagable with said pinion for rotating said pinion.

7. The device of claim 5 wherein said housing includes a locking mechanism to prevent unwanted movement of said housing relative to said rack.

8. The device of claim 4 wherein said housing and said rack each have a portion adapted to be affixed in the oral cavity of a patient.

9. The device of claim 8 wherein said portions are adapted to be affixed to the patient's teeth.

10. The device of claim 8 wherein said portions are adapted to be affixed to adjacent sections of a craniofacial bone of the patient.

11. The device of claim 8 wherein one of said portions is adapted to be affixed to a patient's tooth and the other of said portions is adapted to be affixed to a craniofacial bone of the patient.

12. The device of claim 3 wherein said rack and said pinion each include a set of parallel teeth which are adapted for interengagement.

13. The device of claim 3 wherein said rack and said pinion each include a set of teeth which are adapted for interengagement, said sets of teeth being other than parallel.

14. The device of claim 13 wherein said teeth are conical.

15. The device of claim 1 wherein the craniofacial bone is the mandible and said expandible member is adapted to be affixed on one of either the labial or buccal sides of the mouth.

16. The device of claim 1 wherein said expandable member is curved to provide distraction in more than two planes of space upon activation of said expanding mechanism.

17. A device for bone distraction and movement of teeth, comprising:

an expandible member for affixation in the oral cavity of a patient and adapted to provide movement of a selected craniofacial bone or teeth simultaneously in more than one plane of space, said expandible member including a mechanism for expanding said expandible member, wherein said expanding mechanism comprises a rack and pinion-type device, and wherein said rack includes more than one set of teeth, at least one set of which is adapted for interengagement with said pinion.

18. The device of claim 17 wherein said rack includes two rows of teeth which are laterally offset relative to each other by half a tooth width.

19. The device of claim 18 wherein said pinion is adapted to engage both rows of teeth of said rack.

* * * * *

UNITED STATES PATENT AND TRADEMARK OFFICE
CERTIFICATE OF CORRECTION

PATENT NO. : 6,139,316
DATED : October 31, 2000
INVENTOR(S) : Rohit C. L. Sachdeva et al It is certified that error appears in the above-identified patent and that said Letters Patent is hereby corrected as shown below:

Title page,
The third inventor's name "Lawrence M. Wolford" should be -- Larry M. Wolford -- per the corrected filing receipt.

Signed and Sealed this

Twenty-fifth Day of September, 2001

*Attest:*

*Nicholas P. Godici*

NICHOLAS P. GODICI
*Acting Director of the United States Patent and Trademark Office*

*Attesting Officer*